United States Patent [19]

Abou-Gharbia et al.

[11] Patent Number: 4,957,913

[45] Date of Patent: Sep. 18, 1990

[54] ANTIHYPERTENSIVE POLYCYCLIC IMIDES

[75] Inventors: Magid A. Abou-Gharbia, Glen Mills; Gary P. Stack, Merion; Rodney W. Lappe, Phoenixville, all of Pa.

[73] Assignee: American Home Products Corp., New York, N.Y.

[21] Appl. No.: 440,573

[22] Filed: Nov. 22, 1989

[51] Int. Cl.$^5$ ...................... A61K 31/50; A61K 31/55
[52] U.S. Cl. ..................................... 514/216; 514/253
[58] Field of Search ................................. 514/216, 253

[56] References Cited

U.S. PATENT DOCUMENTS

| | | | |
|---|---|---|---|
| 4,562,255 | 12/1985 | Freed et al. | 544/357 |
| 4,797,488 | 1/1989 | Stack et al. | 544/295 |
| 4,843,678 | 6/1989 | Ishizumi et al. | 514/253 |
| 4,871,738 | 10/1989 | Opitz et al. | 514/252 |
| 4,892,943 | 1/1990 | Abou-Gharbia | 540/575 |

Primary Examiner—Allen J. Robinson
Attorney, Agent, or Firm—Richard K. Jackson

[57] ABSTRACT

Hypertension in the mammal is controlable by administration of a compound of the formula:

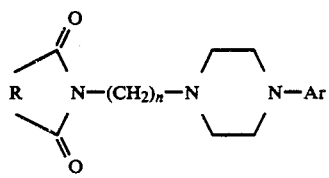

wherein
R is

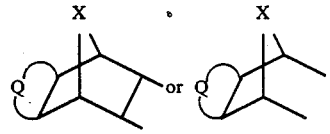

in which
X is methylene, ethylene or ethylidene and Q is alkylene, alkylidene, or Q is a

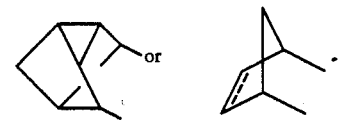

in which the dotted line represents optional unsaturation;
n is one of the integers 2, 3 or 4;
Ar is phenyl or phenyl substituted with halo. trifluoromethyl or alkoxy, or Ar is 2-pyrimidinyl or halopyrimidin-2-yl, 2-pyrazinyl or halo-pyrazin-2-yl, 2-pyridinyl, cyanopyridin-2-yl or halopyridin-2-yl;
or a pharmaceutically acceptable salt thereof.

10 Claims, No Drawings

ANTIHYPERTENSIVE POLYCYCLIC IMIDES

BACKGROUND OF THE INVENTION

U.S. Pat. No. 4,562,255 discloses a group of polycyclic imides which are useful as antihypertensive agents of the formula:

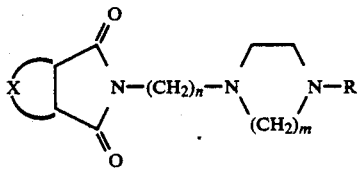

wherein
X is

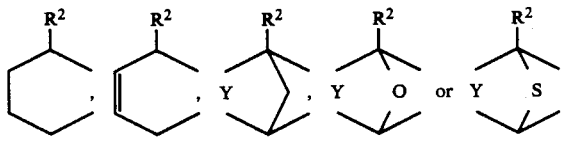

in which
Y represents a single or double bond; and $R^2$ is hydrogen or lower alkyl;
n is one of the integers 2, 3 or 4;
m is one of the integers 1 or 2;
and
R is 2-pyrimidinyl, 2-pyridinyl, 2-pyrazinyl, halo-substituted 2-pyrazinyl, 5-tetrazolyl, phenyl or phenyl substituted by halo, lower alkyl or lower alkoxy groups.

U.S. Pat. No. 4,797,488 discloses a series of polycyclic imides useful as antipsychotics and anxiolytics of the formula:

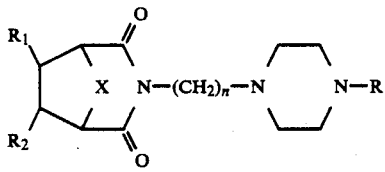

in which
X is $O, S, SO, SO_2, -CR_3R_4$, where $R_3$ and $R_4$, independently, are hydrogen, alkyl of 1 to 4 carbon atoms, or taken together with the carbon atom to which they are joined, $R_3$ and $R_4$ form a cycloalkyl group of 3 to 5 carbon atoms;
n is one of the integers 2-5;
R is phenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, halopyridin-2-yl, cyano-pyridin-2-yl, quinolyl, or haloquinolyl;
$R_1$ and $R_2$, taken together, are alkylene of 3 to 5 carbon atoms or alkenylene of 3 to 5 carbon atoms, or taken with the carbon atoms to which they are attached, $R_1$ and $R_2$ complete a benzene ring, or a group of the formula:

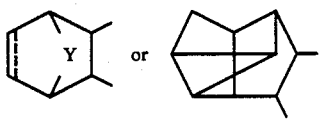

RELATED APPLICATION

U.S. patent application Ser. No. 237,106 discloses some polycyclic imides as useful psychotropic agents of the formula:

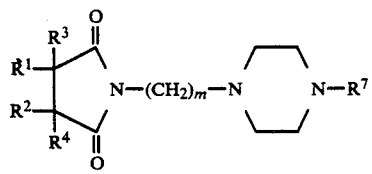

wherein
$R^1$ and $R^2$ represent the structure:

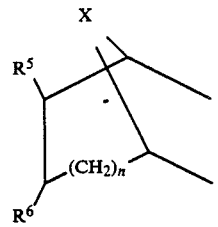

$R^3$ and $R^4$ are hydrogen;
$R^5$ and $R^6$ are hydrogen, or $R^5$ and $R^6$ taken together form a 3-6 membered carbocyclic ring or a cyclobutenyl ring; with the proviso that when $R^3$, $R^4$, $R^5$ and $R^6$ are hydrogen, n is other than zero;
m is 2-4;
n is 0-4;
X is lower alkylene, vinylene or O;
$R^7$ is unsubstituted or monosubstituted phenyl, 2-pyridinyl, 2-pyrimidinyl, 2-pyrazinyl or 3-pyridazinyl; where the substituents are selected from the group lower alkyl, lower alkoxy, halo, cyano, nitro and trifluoromethyl;
and the pharmaceutically acceptable salts thereof.

DESCRIPTION OF THE INVENTION

In accordance with this invention, there is provided a method for treating hypertension which comprises administering to a patient suffering from hypertension, an antihypertensive amount of a compound of the formula:

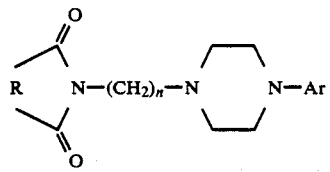

wherein
R is

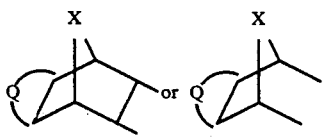

in which
X is methylene, ethylene or ethylidene and Q is alkylene of 1 to 4 carbon atoms, alkylidene of 2 to 4 carbon atoms, or Q is

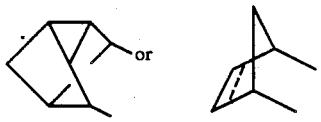

in which the dotted line represents optional unsaturation;
n is one of the integers 2, 3 or 4;
Ar is phenyl or phenyl substituted with halo, trifluoromethyl or alkoxy of 1 to 3 carbon atoms, or Ar is 2-pyrimidinyl or halopyrimidin-2-yl, 2-pyrazinyl or halo-pyrazin-2-yl, 2-pyridinyl, cyanopyridin-2-yl or halopyridin-2-yl;
or a pharmaceutically acceptable salt thereof.

The preferred antihypertensive agents are those in which X and Q are independently ethylene or ethylidene when R is:

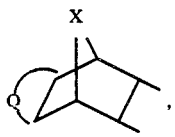

and X is methylene with Q defined in the preceding paragraph when R is:

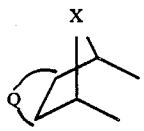

These compounds and their preparation are disclosed in both U.S. Pat. No. 4,797,488 and Ser. No. 237,106. The preparation of the most preferred antihypertensive agents within the group of agents involved in this invention was accomplished as follows:

EXAMPLE 1

2-[4-[4-(6-Chloro-2-pyrazinyl)-1-piperazinyl]butyl]hexahydro-4,6-etheno-cycloprop[f]isoindole-1,3(2H,3aH)-dione, dihydrochloride, sesquihydrate To a stirred solution of 6.8 g (0.035 mol) of 1,3-dioxo-2H-4,6-etheno-1,3,3a,6a-tetrahydrocycloprop[f]isoindole in 70 mL of dimethylformamide is added 0.9 g of sodium hydride. The suspension is stirred at 60° C. for 3 hours and is poured into a stirred solution of 1,4-dibromobutane (9 g, 0.04 mol) in 50 mL of dimethylformamide.

The reaction mixture is stirred at room temperature for 24 hours, dimethylformamide is evaporated under reduced pressure and the residue is extracted with methylene chloride (3×200 mL). The methylene chloride extracts are collected, washed with water, dried over anhydrous Na$_2$SO$_4$ and evaporated under reduced pressure. The residue is solidified to a waxy like material affording 7.6 g (67% yield) of the corresponding 2-(4-bromobutyl)hexahydro-4,6-ethenocycloprop[f]isoindole-1,3-(2H,3aH)-dione. The title compound is prepared by dissolving 2.5 g (0.007 mole) of 2-(4-bromobutylhexahydro-4,6-ethenocycloprop[f]isoindole-1,3(2H,3aH)-dione in 50 mL of dimethylformamide, and to this solution is added 6 mL of triethylamine and 1.7 g (0.007 mL) of 1-(6-chloro-2-pyrazinyl)-piperazine hydrochloride. The reaction mixture is stirred at room temperature for 48 hours. Dimethylformamide is removed under reduced pressure and the remaining solid is extracted with 2×100 mL methylene chloride.

The methylene chloride extracts are dried over anhydrous Na$_2$SO$_4$, evaporated and the title compound is separated by HPLC using 30% methanol-ethyl acetate as eluent. Evaporation of the solvent from the desired fractions (R$_f$0.5) affords 0.95 g (31% yield) of the title compound which is converted to the dihydrochloride salt by dissolving the free base in ethanol and adding ether saturated with hydrogen chloride; m.p. 258°–261° C.

Elemental analysis for C$_{23}$H$_{28}$ClN$_5$O$_2$.2HCl.1½H$_2$O:
Calc'd: C, 50.96; H, 6.09; N, 12.92. Found: C, 50.90; H, 6.09; N, 13.09.

EXAMPLE 2

3a,4,4a,6a,7,7a-Hexahydro-2-[4-[4-(2-pyrimidinyl)-1-piperazinyl]butyl]-4,7-etheno-1H-cyclobut[f]isoindole-1,3(2H)-dione, dihydrochloride, sesquihydrate The title compound is prepared following the procedure of Example 1, using 1,3-dioxo-4,7-etheno-Δ$^5$-1,3,3a,7a-tetrahydrocyclobut[f]isoindole instead of 1,3-dioxo-2H-4,6-etheno-1,3,3a,6a-tetrahydrocycloprop[f]isoindole, and 1-(2-pyrimidinyl)piperazine instead of 1-(6-chloro-2-pyrazinyl)piperazine. The compound is converted to the dihydrochloride salt; m.p. 252°–254° C.

Elemental analysis for C$_{24}$H$_{29}$N$_5$O$_2$.2HCl.1½H$_2$O:
Calc'd: C, 55.44; H, 6.54; N, 13.48. Found: C, 55.00; H, 6.28; N, 13.27.

EXAMPLE 3

2-[4[4-(2-Pyrimidinyl)-1-piperazinyl]butyl]octahydro-4,6-ethanocycloprop[f]isoindole-1,3-(2H,3aH)-dione, dihydrochloride dihydrate The title compound is prepared following the procedure of Example 1 using 1,3-dioxo-2H-4,6-ethano-1,3,3a,5a,6-tetrahydrocycloprop[f]isoindole instead of 1,3-dioxo-2H-4,6-etheno-1,3,3a,6a-tetrahydrocycloprop[f]isoindole and 1-(2-pyrimidinyl)piperazine dihydrochloride instead of 1-(6-chloro-2-pyrazinyl)piperazine hydrochloride. The compound is converted to the dihydrochloride salt; m.p. 190°–192° C.

Elemental analysis for C$_{23}$H$_{31}$N$_5$O$_2$.2HCl.2H$_2$O:
Calc'd: C, 53.24; H, 7.13; N, 13.50. Found: C, 53.41; H, 6.70; N, 13.43.

EXAMPLE 4

2-[4[4-(2-Pyrimidinyl)-1-piperazinyl]butyl]-octahydro-4,7-etheno-1H-cyclobut[f]isoindole-1,3-(2H)-dione, dihydrochloride, hydrate The title compound is prepared following the procedure of Example 1, using 1-(2-pyrimidinyl)piperazine instead of 1-(6-chloro-2-pyrazinyl)piperazine hydrochloride and octahydro-4,7-etheno-1H-cyclobut[f]isoindole-1,3(2H)-dione instead of hexahydro-4,6-ethenocycloprop[f]isoindole-1,3(2H,3aH)-dione and is converted to the hydrochloride salt; m.p. 250°-252° C.

Elemental analysis for $C_{24}H_{31}N_5O_2.2HCl.2H_2O$: Calc'd: C, 56.25; H, 6.83; N, 13.67. Found: C, 56.10; H, 6.66; N, 13.67.

EXAMPLE 5

3a,4,4a,6a,7,7a-Hexahydro-2-[4-[4-(3-chlorophenyl-1-piperazinyl]butyl]-4,7-etheno-1H-cyclobut[f]isoindole-1,3(2H)-dione, dihydrochloride The title compound is prepared following the procedure of Example 1 using 1,3-dioxo-4,7-etheno-$\Delta^5$-1,3,3a,7a-tetrahydrocyclobut[f]isoindole instead of 1,3-dioxo-2H-4,6-etheno-1,3,3a,6a-tetrahydrocycloprop[f]isoindole, and 1-(3-chlorophenyl)piperazine instead of 1-(6-chloro-2-pyrazinyl)piperazine. The compound is converted to the dihydrochloride salt; m.p. 225°-227° C.

Elemental analysis for $C_{26}H_{30}N_3ClO_2.2HCl$: Calc'd: C, 59.43; H, 6.10; N, 8.00. Found: C, 59.23; H, 6.23; N, 8.01.

EXAMPLE 6

4,4a,5,5a,6,6a-Hexahydro-2-[4-[4-(2-pyrimidinyl)-1-piperazinyl]butyl]-4,6-ethenocycloprop[f]isoindole-1,3-(2H,3aH)-dione, dihydrochloride The title compound is prepared following the procedure of Example 1 using 1-(2-pyrimidinyl)piperazine dihydrochloride instead of 1-(6-chloro-2-pyrazinyl)piperazine hydrochloride and is converted to the dihydrochloride salt; m.p. 207°-208° C.

Elemental analysis for $C_{23}H_{29}N_5O_2.2HCl.H_2O$: Calc'd: C, 55.42; H, 6.62; N, 14.0; C, 14.25. Found: C, 54.92; H, 6.42; N, 13.60; Cl, 14.38.

EXAMPLE 7

Decahydro-3-[4-[4-(2-pyrimidinyl)-1-piperazinyl]butyl]-1,5-methano-6,7,9-methano-2H-pentaleno[1,2-d]azepine-2,4(3H)-dione Potassium permangante (50 g, 0.32 moles) was dissolved in 500 mL of water in a 1 liter three neck flask equipped with a thermometer, addition funnel and overhead stirrer. To it was added a solution of 18.4 g (0.10 mole) of norbornadiene dimer and 5.0 g (0.018 mole) of tetra-n-butylammonium chloride in 300 mL of benzene. The internal temperature was kept below 40° C. by means of a cold water bath. The reaction was stirred overnight at room temperature; then 60 g of sodium bisulfite was added and the mixture acidified with concentrated hydrochloric acid. Five-hundred milliliters of ethyl acetate was added and the organic phase was removed in a separatory funnel. The aqueous phase was extracted with two additional 500 mL portions of ethyl acetate. The combined organic portions were washed with 300 mL saturated brine, dried over $Na_2SO_4$, filtered, and evaporated to obtain 24 g of 2,3,3a,4,5,6,6a,7,7a-decahydro-4,6,7-metheno-1H-cyclopenta[a]pentalene-1,3-dicarboxylic acid.

The diacid prepared above (2.5 g, 10 mmoles) was combined with 2.4 g (10 mmoles) of 1-(4-aminobutyl)-4-(2-pyrimidinyl)piperazine in 300 mL of xylene and refluxed under $N_2$ for 48 hours with water separation via a Dean-Stark trap. The mixture was allowed to cool, concentrated in vacuum and filtered through 75 g of silica gel in 2% $EtOH/CHCl_3$. Concentration in vacuum and recrystallization from isopropanol with the addition of 4N HCl/isopropanol gave a pale pink solid title compound as the dihydrochloride, hemihydrate, 820 mg; m.p. 229°-231° C.

Elemental analysis for $C_{26}H_{33}N_5O_2.2HCl.\frac{1}{2}H_2O$: Calc'd: C, 58.98; H, 6.85; N, 13.23. Found: C, 59.26; H, 6.78; N, 13.04.

These compounds were shown to be effective in lowering arterial blood pressure in standard tests using hypertensive rats. The tests were conducted on spontaneously hypertensive rats, with test and control groups consisting of 6 rats, and the compounds being administered orally. Mean arterial blood pressure was measured continuously through an indwelling cannula surgically implanted in the femoral artery. Readings were taken prior to drug administration and changes in mean arterial pressure and heart rate were continuously monitored for at least 10 hours after dosing. Data are grouped and summarized with mean change in arterial pressure and heart rate calculated for each hour postdosing.

When administered at 25 mg/kg, the compounds demonstrated a significant ability to reduce arterial pressure and heart rate. When tested in spontaneously hypertensive rats as described above, the compounds gave the following results:

| | | Maximal Change | |
|---|---|---|---|
| Example | Dose | Mean Arterial Pressure (mm Hg) | Heart Rate (beats/min) |
| 1 | 25 mg/kg | | |
| 2 | 25 mg/kg | −47 | −98 |
| 3 | 25 mg/kg | −21 | −86 |
| 4 | 25 mg/kg | −26 | −38 |
| 5 | 25 mg/kg | −30 | −62 |
| 6 | 25 mg/kg | −26 | −56 |
| 7 | 25 mg/kg | −44 | −108 |

Thus, the compounds employed in the process of this invention were established to be potent antihypertensive agents. As such, this may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid from compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific antihypertensive state must be subjectively determined by the attending physician. The variables involved include the degree of hypertension and the size, age and response pattern of the patient. Based upon the activity profile and potency of the compounds tested, supra, an initial human dose within the range of about 10 to about 50 mg/kg/day, by single or divided, oral administration, should be appropriate. The containing dose may then be modified to achieve the desired effect, within the range of about 5 to about 100 mg/day, as personalized for the patient.

What is claimed is:

1. A method for lowering blood pressure which comprises administering to a hypertensive mammal, an antihypertensive amount of a compound of the formula:

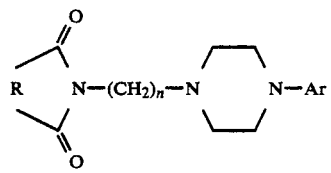

wherein

R is

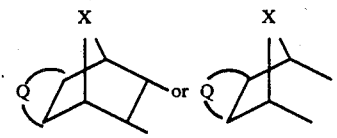

in which

X is methylene, ethylene or ethylidene and Q is alkylene of 1 to 4 carbon atoms, alkylidene of 2 to 4 carbon atoms, or Q is

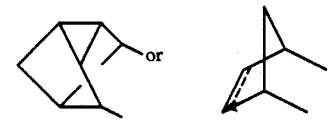

in which the dotted line represents optional unsaturation;

n is one of the integers 2, 3 or 4;

Ar is phenyl or phenyl substituted with halo, trifluoromethyl or alkoxy of 1 to 3 carbon atoms, or Ar is 2-pyrimidinyl or halopyrimidin-2-yl, 2-pyrazinyl, or halo-pyrazin-2-yl, 2-pyridinyl, cyanopyridin-2-yl or halopyridin-2-yl;

or a pharmaceutically acceptable salt thereof.

2. A method for lowering blood pressure as claimed in claim 1 which comprises administering to a hypertensive mammal, an antihypertensive amount of a compound of the formula:

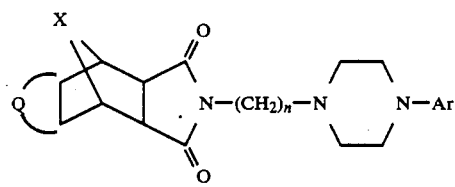

in which

Q is ethylene or ethylidine;

X is ethylene or ethylidine;

Ar is phenyl or phenyl substituted with halo, trifluoromethyl or alkoxy of 1 to 3 carbon atoms, or Ar is 2-pyrimidinyl or halopyrimidin-2-yl, 2-pyrazinyl or halo-pyrazin-2-yl, 2-pyridinyl, cyanopyridin-2-yl or halopyridin-2-yl;

n is one of the integers 2, 3 or 4;

or a pharmaceutically acceptable salt thereof.

3. A method for lowering blood pressure as claimed in claim 1 which comprises administering to a hypertensive mammal, an antihypertensive amount of a compound of the formula:

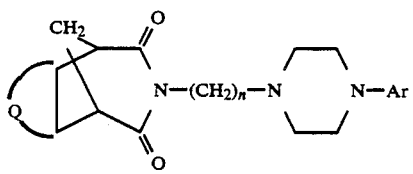

in which

Q is alkylene of 1 to 4 carbon atoms, alkylidene of 2 to 4 carbon atoms, or Q is

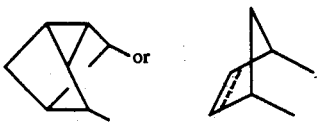

in which the dotted line represents optional unsaturation;

Ar is phenyl or phenyl substituted with halo, trifluoromethyl or alkoxy of 1 to 3 carbon atoms, or Ar is 2-pyrimidinyl or halopyrimidin-2-yl, 2-pyrazinyl or halo-pyrazin-2-yl, 2-pyridinyl, cyanopyridin-2-yl or halopyridin-2-yl;

n is one of the integers 2, 3 or 4;

or a pharmaceutically acceptable salt thereof.

4. A method of claim 1 in which said compound is 2-[4-[4-(6-chloro-2-pyrazinyl)-1-piperazinyl]butyl]hexahydro-4,6-etheno-cycloprop[f]isoindole-1,3(2H,3aH)-dione, or a pharmaceutically acceptable salt thereof.

5. A method of claim 1 in which said compound is 3a,4,4a,6a,7,7a-hexahydro-2-[4-[4-(2-pyrimidinyl)-1-piperazinyl]butyl]-4,7-etheno-1H-cyclobut[f]isoindole-1,3(2H)-dione, or a pharmaceutically acceptable salt thereof.

6. A method of claim 1 in which said compound is 2-[4-[4-(2-pyrimidinyl)-1-piperazinyl]butyl]octahydro-4,6-ethanocycloprop[f]isoindole-1,3-(2H,3aH)-dione, or a pharmaceutically acceptable salt thereof.

7. A method of claim 1 in which said compound is 2-[4-[4-(2-pyrimidinyl)-1-piperazinyl]butyl]-octahydro-4,7,etheno-1H-cyclobut[f]isoindole-1,3-(2H)-dione, or a pharmaceutically acceptable salt thereof.

8. A method of claim 1 in which said compound is 3a,4,4a,6a,7,7a-hexahydro-2-[4-[4-(3-chlorophenyl-1-piperazinyl]butyl]-4,7-etheno-1H-cyclobut[f]isoindole-1,3(2H)-dione, or a pharmaceutically acceptable salt thereof.

9. A method of claim 1 in which said compound is 4,4a,5,5a,6,6a-hexahydro-2-[4-[4-(2-pyrimidinyl)-1-piperazinyl]butyl]-4,6-ethenocycloprop[f]isoindole-1,3-(2H,3aH)-dione, or a pharmaceutically acceptable salt thereof.

10. A method of claim 1 in which said compound is decahydro-3-[4-[4-(2-pyrimidinyl)-1-piperazinyl]butyl]-1,5-methano-6,7,9-metheno-2H-pentaleno[1,2-d]azepine-2,4(3H)-dione, or a pharmaceutically acceptable salt thereof.

* * * * *